(12) United States Patent
Philipak et al.

(10) Patent No.: US 10,172,545 B2
(45) Date of Patent: Jan. 8, 2019

(54) ADAPTER CAPS FOR SAMPLE COLLECTION CONTAINERS AND ASSOCIATED MOLDS WITH CORE PINS AND RELATED METHODS

(71) Applicant: bioMérieux, Inc., Durham, NC (US)

(72) Inventors: Stanley M. Philipak; Samuel B. Crandall, Troy, MO (US)

(73) Assignee: bioMérieux, Inc., Durham, NC (US)

( * ) Notice: Subject to any disclaimer, the term of this patent is extended or adjusted under 35 U.S.C. 154(b) by 552 days.

(21) Appl. No.: 14/259,591

(22) Filed: Apr. 23, 2014

(65) Prior Publication Data

US 2014/0322104 A1     Oct. 30, 2014

Related U.S. Application Data

(60) Provisional application No. 61/815,395, filed on Apr. 24, 2013.

(51) Int. Cl.
| | |
|---|---|
| *A61B 5/15* | (2006.01) |
| *B29C 45/44* | (2006.01) |
| *A61J 1/20* | (2006.01) |
| *A61B 5/154* | (2006.01) |

(52) U.S. Cl.
CPC .... *A61B 5/150351* (2013.01); *A61B 5/15003* (2013.01); *A61B 5/154* (2013.01); *A61B 5/150274* (2013.01); *A61B 5/150992* (2013.01); *A61J 1/2096* (2013.01); *B29C 45/44* (2013.01)

(58) Field of Classification Search
CPC ........ B01L 3/56; B01L 3/561; B01L 2200/02; B01L 2200/023; B01L 2200/085; A61B 5/150274; A61B 5/150351

USPC .......................................... 422/544, 546, 568
See application file for complete search history.

(56) References Cited

U.S. PATENT DOCUMENTS

| | | | |
|---|---|---|---|
| 4,827,944 A | 5/1989 | Nugent | |
| 4,945,060 A | 7/1990 | Turner et al. | |
| 5,000,804 A | 3/1991 | Nugent | |
| 5,094,955 A | 3/1992 | Calandra et al. | |
| 5,162,229 A | 11/1992 | Thorpe et al. | |
| 5,164,796 A | 11/1992 | Di Guiseppi et al. | |
| 5,217,876 A | 6/1993 | Turner et al. | |
| 5,344,417 A | 9/1994 | Wadsworth, Jr. | |
| 5,360,423 A | 11/1994 | McCormick | |
| 5,374,264 A | 12/1994 | Wadsworth, Jr. | |
| 5,770,394 A | 6/1998 | Berndt | |
| 5,795,773 A | 8/1998 | Read et al. | |

(Continued)

FOREIGN PATENT DOCUMENTS

WO    WO1994/026874    11/1994

OTHER PUBLICATIONS

BacT/ALERT® Blood Collection Adapter, bioMérieux, Inc., Product Insert, 3 pages, Apr. 2004.

*Primary Examiner* — Jill A Warden
*Assistant Examiner* — Dwayne K Handy
(74) *Attorney, Agent, or Firm* — Myers Bigel, P.A.

(57) ABSTRACT

Adapter caps for sample collection containers have a monolithic elongate body with an upper neck portion that merges into a larger lower body portion with an open internal cavity. The upper neck portion has an open needle bore that is concentrically aligned with the open internal cavity. The monolithic elongate body has an axially extending centerline. The needle bore has a downwardly extending wall with an inner surface that comprises a plurality of circumferentially spaced apart longitudinally extending flat surfaces.

21 Claims, 10 Drawing Sheets

(56) References Cited

U.S. PATENT DOCUMENTS

| | | |
|---|---|---|
| 5,856,175 A | 1/1999 | Thorpe et al. |
| 5,860,329 A | 1/1999 | Day |
| D427,308 S | 6/2000 | Zinger |
| 6,123,211 A | 9/2000 | Rashid et al. |
| 6,537,263 B1 | 3/2003 | Aneas |
| 6,709,857 B2 | 3/2004 | Bachur, Jr. |
| 6,997,916 B2 | 2/2006 | Simas, Jr. et al. |
| 7,211,430 B2 | 5/2007 | Schwarz et al. |
| 7,261,698 B2 | 8/2007 | Sampson et al. |
| D588,691 S | 3/2009 | Sampson et al. |
| D617,894 S | 6/2010 | Wright |
| D686,322 S | 7/2013 | Maeda et al. |
| D720,452 S | 12/2014 | Jordan |
| D737,960 S | 9/2015 | Philipak et al. |
| 2004/0215106 A1 | 10/2004 | Sampson et al. |
| 2005/0037165 A1 | 2/2005 | Ahern et al. |
| 2010/0068755 A1 | 3/2010 | Walsh |
| 2011/0081714 A1 | 4/2011 | Wilson et al. |
| 2011/0124028 A1 | 5/2011 | Robinson et al. |
| 2012/0323221 A1 | 12/2012 | Gallo et al. |
| 2013/0313287 A1 | 11/2013 | Walsh et al. |
| 2014/0088544 A1 | 3/2014 | Yow et al. |
| 2014/0322104 A1 | 10/2014 | Philipak et al. |

ADAPTER CAP INSERT NEEDLE (OLD AND NEW) THREAD COMPARISONS

OLD DRAW NEEDLE #1

EXTERNAL THREADS READINGS
| INCHES | mm |
|---|---|
| 0.1831 | 4.651 |
| 0.1839 | 4.671 |
| 0.1850 | 4.699 |

INTERNAL THREADS READINGS
| INCHES | mm |
|---|---|
| 0.1344 | 3.414 |
| 0.1330 | 3.378 |
| 0.1328 | 3.373 |

PITCH
| INCHES | mm |
|---|---|
| 0.0618 | 1.570 |
| 0.0617 | 1.567 |

LOT# UNKNOWN
EXPIRATION DATE UNKNOWN

OLD DRAW NEEDLE #2

EXTERNAL THREADS READINGS
| INCHES | mm | AVERAGE |
|---|---|---|
| 0.1835 | 4.661 | 4.663 |
| 0.1843 | 4.681 | |
| 0.1818 | 4.618 | |

INTERNAL THREADS READINGS
| INCHES | mm | AVERAGE |
|---|---|---|
| 0.1350 | 3.429 | 3.392 |
| 0.1322 | 3.358 | |
| 0.1338 | 3.399 | |

PITCH
| INCHES | mm |
|---|---|
| 0.0622 | 1.580 |
| 0.0615 | 1.562 |

LOT# UNKNOWN
EXPIRATION DATE UNKNOWN

NEW DRAW NEEDLE

EXTERNAL THREAD READING
| INCHES | mm | AVERAGE |
|---|---|---|
| 0.1755 | 4.458 | 4.425 |
| 0.1735 | 4.407 | |
| 0.1736 | 4.409 | |

INTERNAL THREADS READINGS
| INCHES | mm | AVERAGE |
|---|---|---|
| 0.1288 | 3.272 | 3.250 |
| 0.1276 | 3.241 | |
| 0.1274 | 3.236 | |

PITCH
| INCHES | mm |
|---|---|
| 0.0549 | 1.394 |
| 0.0554 | 1.407 |

LOT# 1H0891
EXPIRATION DATE 2014-08

FIG. 12A

2ND MEASUREMENTS

OLD DRAW NEEDLE #1

EXTERNAL THREADS READINGS

| INCHES | mm |
|---|---|
| 0.1845 | 4.686 |
| 0.1852 | 4.704 |
| 0.1837 | 4.666 |

INTERNAL THREADS READINGS

| INCHES | mm |
|---|---|
| 0.1353 | 3.437 |
| 0.1341 | 3.406 |
| 0.1366 | 3.470 |

PITCH

| INCHES | mm |
|---|---|
| 0.0610 | 1.549 |
| 0.0609 | 1.547 |

LOT# UNKNOWN
EXPIRATION DATE UNKNOWN

OLD DRAW NEEDLE #2

EXTERNAL THREADS READINGS

| INCHES | mm | AVERAGE |
|---|---|---|
| 0.1860 | 4.724 | 4.696 |
| 0.1852 | 4.704 | |
| 0.1847 | 4.691 | |

INTERNAL THREADS READINGS

| INCHES | mm | AVERAGE |
|---|---|---|
| 0.1341 | 3.406 | 3.424 |
| 0.1341 | 3.406 | |
| 0.1346 | 3.419 | |

PITCH

| INCHES | mm |
|---|---|
| 0.0623 | 1.582 |
| 0.0629 | 1.598 |

LOT# UNKNOWN
EXPIRATION DATE UNKNOWN

NEW DRAW NEEDLE #1

EXTERNAL THREADS READINGS

| INCHES | mm |
|---|---|
| 0.1776 | 4.511 |
| 0.1781 | 4.524 |
| 0.1783 | 4.529 |

INTERNAL THREADS READINGS

| INCHES | mm |
|---|---|
| 0.1316 | 3.343 |
| 0.1323 | 3.360 |
| 0.1328 | 3.373 |

PITCH

| INCHES | mm |
|---|---|
| 0.0538 | 1.367 |
| 0.0542 | 1.377 |

LOT# 1H0891
EXPIRATION DATE 2014-08

NEW DRAW NEEDLE #2

EXTERNAL THREADS READINGS

| INCHES | mm | AVERAGE |
|---|---|---|
| 0.18 | 4.514 | 4.511 |
| 0.18 | 4.491 | |
| #### | 4.496 | |

IINTERNAL THREAD READING

| INCHES | mm | AVERAGE |
|---|---|---|
| #### | 3.381 | 3.353 |
| #### | 3.317 | |
| #### | 3.345 | |

PITCH

| INCHES | mm |
|---|---|
| #### | 1.422 |
| #### | 1.415 |

LOT# 1H0891
EXPIRATION DATE 2014-08

FIG. 12B

ADAPTER CAPS FOR SAMPLE COLLECTION CONTAINERS AND ASSOCIATED MOLDS WITH CORE PINS AND RELATED METHODS

RELATED APPLICATIONS

This application claims the benefit of and priority to U.S. Provisional Application Ser. No. 61/815,395, filed Apr. 24, 2013, the contents of which are hereby incorporated by reference as if recited in full herein.

FIELD OF THE INVENTION

The instant invention relates to the collection of biological fluid specimens and particularly the collection of bodily fluids such as, for example, blood from a patient and the transfer of the bodily fluid from the patient to fluid collection containers.

BACKGROUND OF THE INVENTION

A biosample such as blood can be withdrawn from a patient and stored in a culture collection bottle. Bottles for collection and culturing of blood and other biological or industrial samples are known in the art. See, e.g., U.S. Pat. Nos. 4,945,060; 5,094,955; 5,860,329; 4,827,944; 5,000,804; 6,123,211; 7,211,430 and U.S. Patent Publication Nos. 2005/0037165 and 2011/0081714, the contents of which are incorporated by reference as if recited in full herein.

To collect blood, an intravenous needle is inserted to the vein of the patient after it is connected to an adapter cap to which the top of the blood culture bottle can be mated. Examples of such holders are described in U.S. Pat. Nos. 5,374,264; 7,261,698 and 5,360,423, the contents of which are hereby incorporated by reference as if recited in full herein. An example of a commercially available adapter cap is the Saf-T Holder® adapter cap from bioMérieux, Inc., Durham, N.C. The adapters can prevent accidental needle pricks of a contaminated needle. The adapter cap is attached to the culture collection bottle and pressed down so that the needle held in the needle bore of the adapter cap penetrates the septum of the collection container and initiates blood flow into the collection bottle.

Despite the above, there remains a need for cost-effective adapter caps that can accommodate and seal to multiple needles from different manufacturers.

SUMMARY OF EMBODIMENTS OF THE INVENTION

Embodiments of the invention are directed to adapter caps for sample collection containers. The adapter caps have a needle bore with a plurality of longitudinally extending flat surfaces.

Embodiments of the invention are directed to adapter caps for a sample collection container. The adapter caps include a monolithic elongate body having an upper neck portion with an open needle bore. The needle bore has a downwardly extending wall with an inner surface that includes (i) a plurality of circumferentially spaced apart longitudinally extending flat surfaces and (ii) first and second circumferentially spaced apart threads that extend radially inward from the inner surface so that respective innermost edges reside on opposing sides of an axially extending centerline of the elongate body.

The upper neck portion can merge into a larger lower body portion with an open internal cavity. The upper neck portion can be concentrically aligned with the open internal cavity.

The flat surfaces can extend a distance above and below the threads.

The threads can have a respective injection molded thread configuration and the thread on one side of the needle bore resides above the thread on an opposing side of the needle bore.

The plurality of flat surfaces can be between 2-6 flat surfaces.

The elongate body can include a molded polymeric material with a substantially constant wall thickness of between about 0.5 mm to about 2 mm.

The wall thickness can be about 1 mm.

The polymeric material can be polypropylene.

The flat surfaces can define wall segments with increased wall thickness of between 0.01 mm and 0.03 mm, average, relative to adjacent segments of the inner wall.

The plurality of longitudinally extending flat surfaces can be four flat surfaces that are symmetrically circumferentially spaced apart.

The plurality of longitudinally extending flat surfaces can have a common substantially constant width that is between about 5%-30% of a major diameter of the needle bore.

The needle bore can have a major diameter of about 4.60 mm.

The plurality of longitudinally extending flat surfaces can have a width that is between about 0.25 mm to about 1 mm.

At least some of the flat surfaces can have a length that is between about 2-2.8 mm.

The needle bore can have a major diameter of about 4.60 mm. Opposing pairs of the longitudinally extending flat surfaces can have a thickness sufficient to define a nominal diameter therebetween of about 4.40 mm.

The adapter cap can include a culture collection container with an upper portion thereof residing in the cavity of the elongate body under the needle bore.

Some embodiments are directed to an injection mold assembly. The assembly includes: (a) an injection mold cavity defining a shape of an adapter cap having an elongate body with an upper neck portion that merges into a larger lower body portion with an open internal cavity; and (b) a core pin having a length in the mold cavity, the core pin having a segment with a reduced diameter that extends to an end thereof. The end has an external thread configuration. The reduced diameter segment has a plurality of longitudinally extending spaced apart flat surfaces.

The core pin flat surfaces can terminate prior to the thread configuration and/or extend longitudinally above and below the thread configuration.

The mold assembly can also include a cavity pin having a length that is less than the length of the core pin, aligned with the core pin in the mold cavity.

The cavity pin can have an end portion with a reduced diameter that extends to an end thereof. The end can have a thread configuration. The reduced diameter segment can have a plurality of longitudinally extending spaced apart flat surfaces that terminate prior to the thread configuration.

The core pin and the cavity pin can be configured to reside in the mold cavity with aligned flat surfaces across the respective ends to define an injection molded needle bore inner surface with longitudinally extending flat surfaces.

The core pin flat surfaces can longitudinally extend a distance between about 0.10 mm-0.11 mm.

The plurality of flat surfaces can define an outer surface with a nominal diameter that is less than a nominal diameter of adjacent outer surface segments by between 5-10%.

Still other embodiments are directed to methods of fabricating an adaptor cap. The methods include: (a) providing an injection mold cavity; (b) placing a core pin in the mold cavity, wherein the core pin has an end portion with a plurality of longitudinally extending spaced apart flat surfaces and a thread configuration; (c) introducing a moldable polymer material into the injection mold cavity having the core pin; (d) injection molding a monolithic adapter cap with a needle bore having threads and longitudinally extending flat surfaces; and (e) using a straight pull to remove the core pin thereby exposing the injection molded adapter cap with the needle bore without requiring spinning to form the threads.

The method can also include placing a cavity pin in the mold cavity aligned with the core pin. The cavity pin can optionally have a plurality of longitudinally extending spaced apart flat surfaces and a thread configuration.

The injection molding can be carried out to form a needle bore having longitudinally extending flat surfaces that extend above and below the threads.

The collection container body can have a wall thickness of between about 1-5 mm (on average). The container body can be a transparent polycarbonate body or a transparent cyclic olefin copolymer body.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

DETAILED DESCRIPTION OF EMBODIMENTS OF THE INVENTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment even if not explicitly described or shown with another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "about" means that the recited number or value can vary by +/−20%.

The term "thread" and derivatives thereof refers to a helical structural thread feature that attaches to a threaded needle component.

The term "sample" refers to a target material undergoing testing or analysis for content. The sample can be a food sample, an environmental sample (water, air, soil, etc.) or a biosample. The testing can be for quality control of food produced in a commercial manufacturing facility, for the EPA (Environmental Protection Agency of the U.S. Government), for environmental toxins or hazardous materials that are man-made, intentional or not, or medical (clinical diagnostic) purposes.

The term "biosample" refers to human or animal tissue, blood, blood plasma or serum, blood fractions, joint fluid, urine, semen, saliva, feces, cerebrospinal fluid, gastric contents, vaginal secretions, tissue homogenates, bone marrow aspirates, bone homogenates, sputum or lavages, aspirates, swabs and swab rinsates, blood products (e.g., platelets, serum, plasma, white blood cell fractions, etc.), donor organ or tissue samples, and the like. In one embodiment, the biological sample tested is a blood sample, urine, cerebral spinal fluid, lavages, mucus or other solid or liquid samples for analysis which may have microbes, microorganisms, toxins and/or cellular material or other constituents of interest. Embodiments of the invention may be suitable for veterinarian use, medical human use or research for human and/or with laboratory animals.

In general, the adapters and cooperating containers can be used for any known test sample (e.g., a biological sample or specimen). For example, the test sample can be a clinical or non-clinical sample suspected of containing one or more microbial agents. Other samples that may be tested include, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, and fruit) and biowarfare samples.

The term "sterile" and derivatives thereof mean that the noted device or material meets or exceeds defined (e.g., food or medical) guidelines of sterility so as to be substantially (if not totally) free of contaminants for at least a defined shelf life so as to be suitable for intended uses, e.g., clinical, health, or consumer product testing for the presence of toxins, microbes, microorganisms or other target constituents in a sample undergoing analysis. The sample can undergo analysis while held in the container. The sample may be transferred after transport and/or culturing in the container for analysis.

The term "aseptic" is used interchangeably with the word "sterile." In some embodiments, the aseptic processing or fabrication complies with GMP (Good Manufacturing Practice) industry guidelines such as those associated with Guidance for Industry—Sterile Drug Products Produced by Aseptic Processing—Current Good Manufacturing Practice, U.S. Department of Health and Human Services Food and Drug Administration, September 2004.

The term "automatic" means that the operation can be carried out using automated electromechanical equipment, rather than with manual labor.

Embodiments of the invention provide an economic adapter cap 10 that can accommodate needles from a plurality of different manufacturers, which can have different tolerances and dimensions, in a manner that maintains sufficient engagement of the needle in the needle bore when punctured through the septum of a collection container during use.

Figure 1:
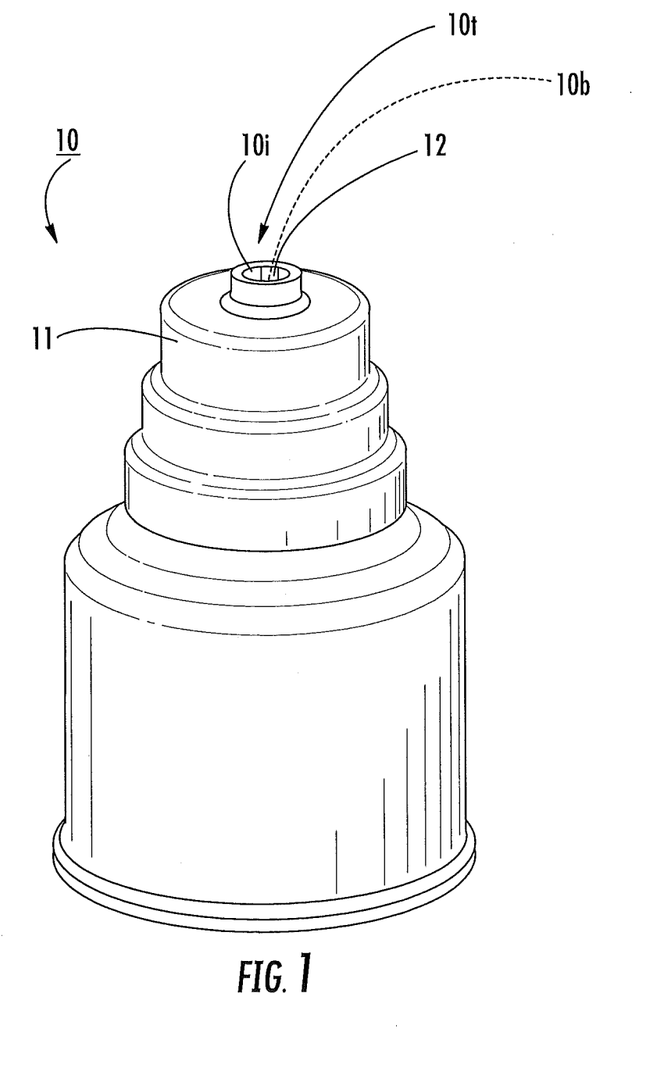
FIG. 1 is a front perspective view of an exemplary adapter cap according to embodiments of the present invention.
Figure 2:
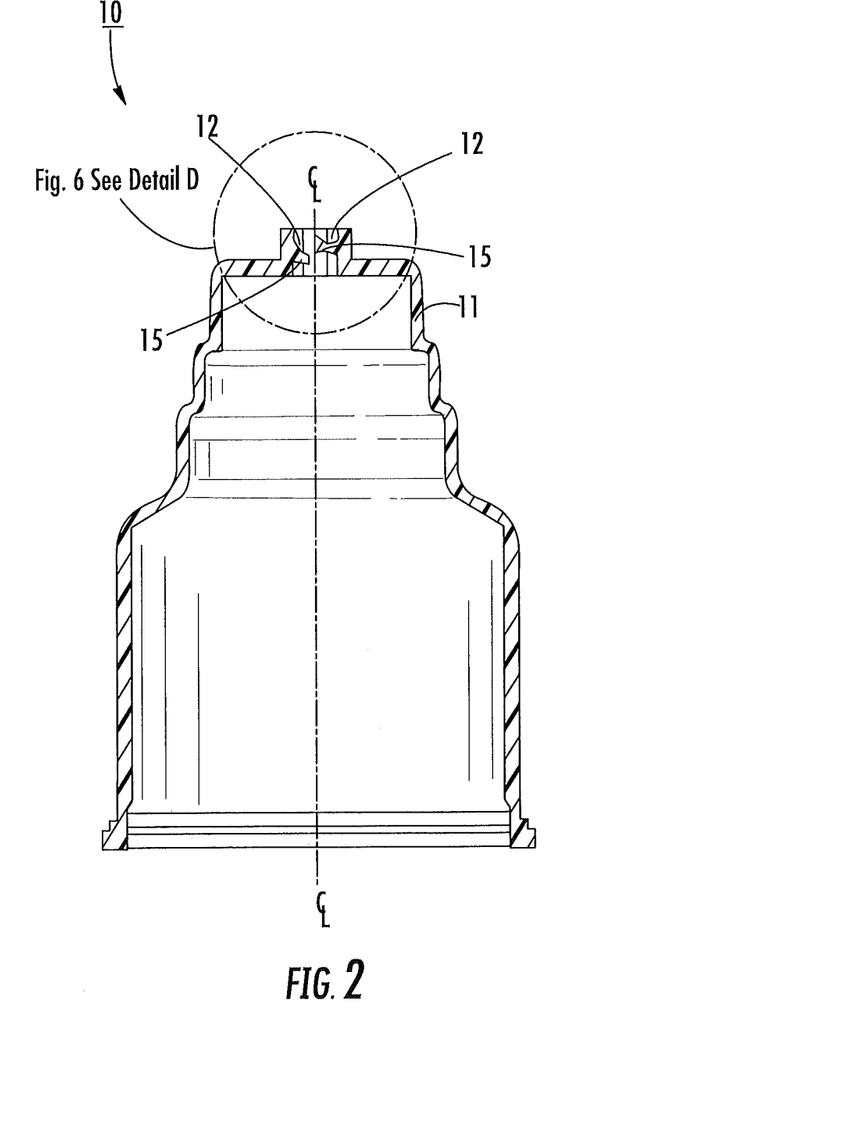
FIG. 2 is a section view of the adapter cap shown in FIG. 1 taken along lines 2-2 of FIG. 5.
Figure 11:
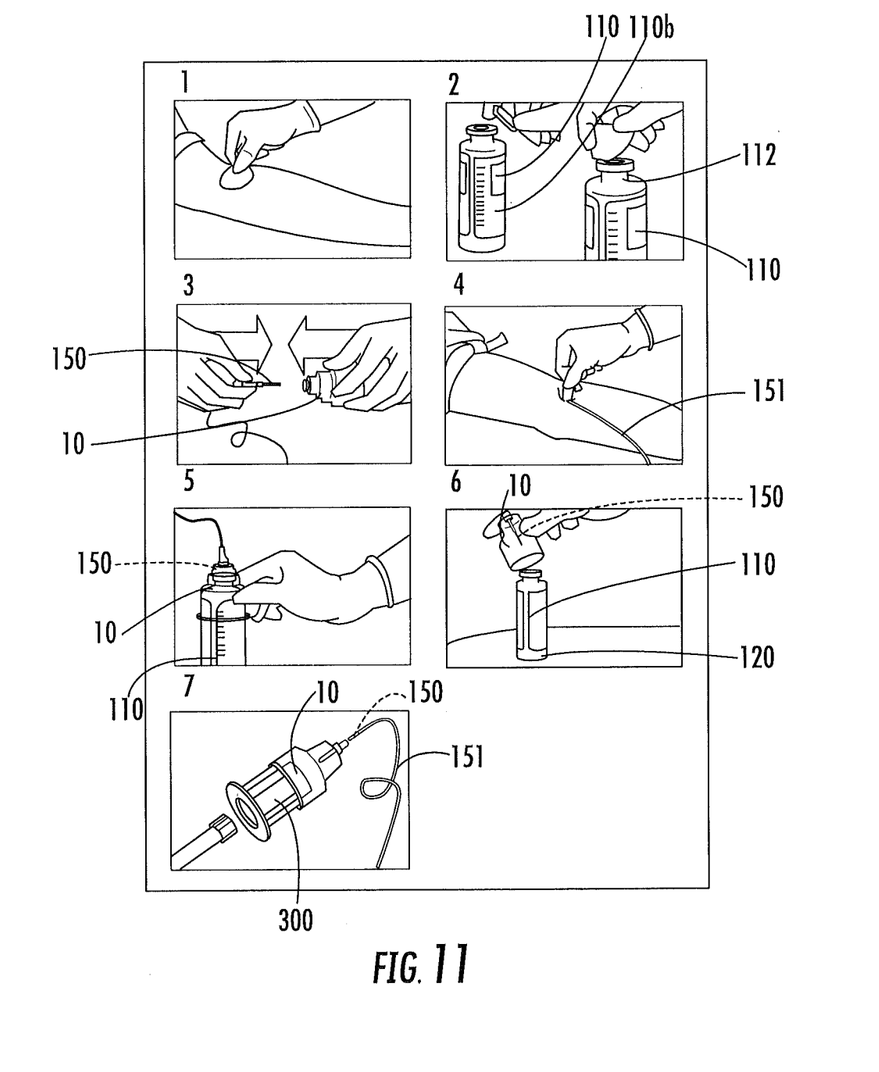
FIG. 11 is a schematic illustration of a series of actions that can be carried out using the adapter cap according to embodiments of the present invention.

Turning now to the figures, FIGS. 1-7 illustrate an adapter cap 10 with a tip 10t defining a needle bore 10b with a plurality of longitudinally extending flat surfaces 12 on an inner surface 10i of a wall of the needle bore. As shown in FIGS. 1 and 2, for example, the cap 10 has an elongate body. The cap 10 can have a series of decreasing diameter outer wall segments from a bottom to the top thereof. The cap 10 can have various form factors and shapes and is not limited to the body shape shown. The cap 10 can have a smaller upper neck portion that provides the needle bore. The neck portion merges into a larger lower portion that is sized and configured to receive an upper portion of a collection container 110 (FIG. 11).

As shown in FIG. 2, the cap 10 can have a wall 11 with a substantially constant wall thickness. The cap can be a monolithic, injection molded cap with a single piece construction.

The plurality of flat surfaces 12 are circumferentially spaced apart and can include between 2-10 longitudinally extending flat surfaces 12, typically between 3-6, such as 3, 4, 5 and 6 flat surfaces 12. The flat surfaces 12 can be arranged so that at least one resides on each side of a centerline (c/L) of the needle bore 10b and cap 10.

Figures 5, 6, 7:
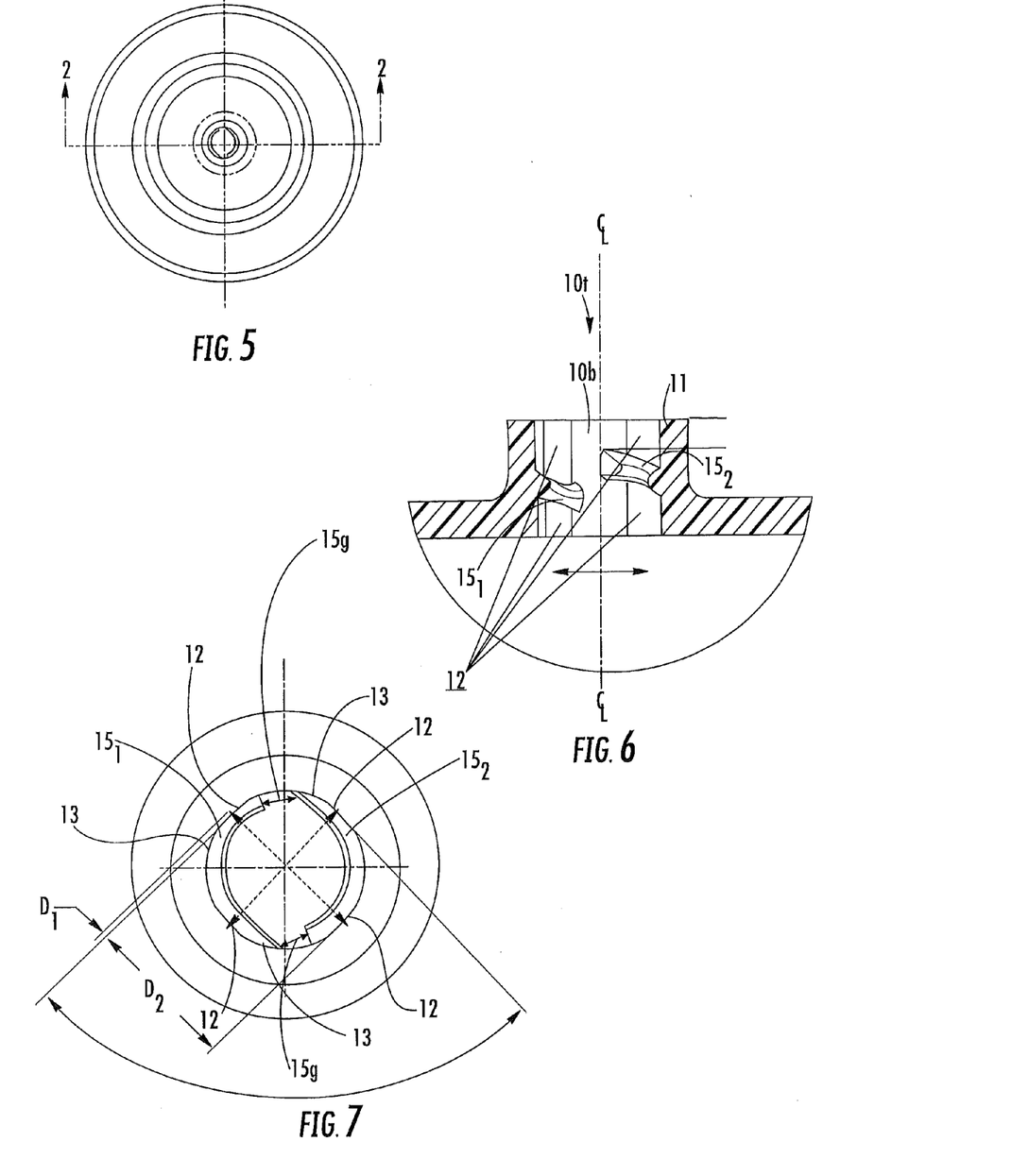
FIG. 5 is a top enlarged view of the adapter cap shown in FIG. 1.
FIG. 6 is an enlarged section view of Detail D of FIG. 2 according to embodiments of the present invention.
FIG. 7 is an enlarged view of a top medial portion of the adapter cap shown in FIG. 5 according to embodiments of the present invention.

The cap 10 can also include two or more internal opposing threads 15. The threads 15 can extend inwardly to reside on opposing sides of an axially extending centerline (c/L) of the needle bore 10b. One thread 15$_2$ can be closely spaced above the other 15$_1$ (FIG. 6). The threads 15 can be sized and configured to engage luer threads of a collection needle set used to carry out the collection even accounting for dimensional variations manufacturer to manufacturer and/or lot-to-lot. The innermost ends of the threads 15 can define a nominal diameter therebetween of about 3.60 inches. The inner wall 10i can have a circumferentially extending gap space 15g between the first and second threads 15$_1$, 15$_2$ as shown in FIG. 7. The pitch of the thread 15$_1$ can be about 2.8 mm.

Figure 3:
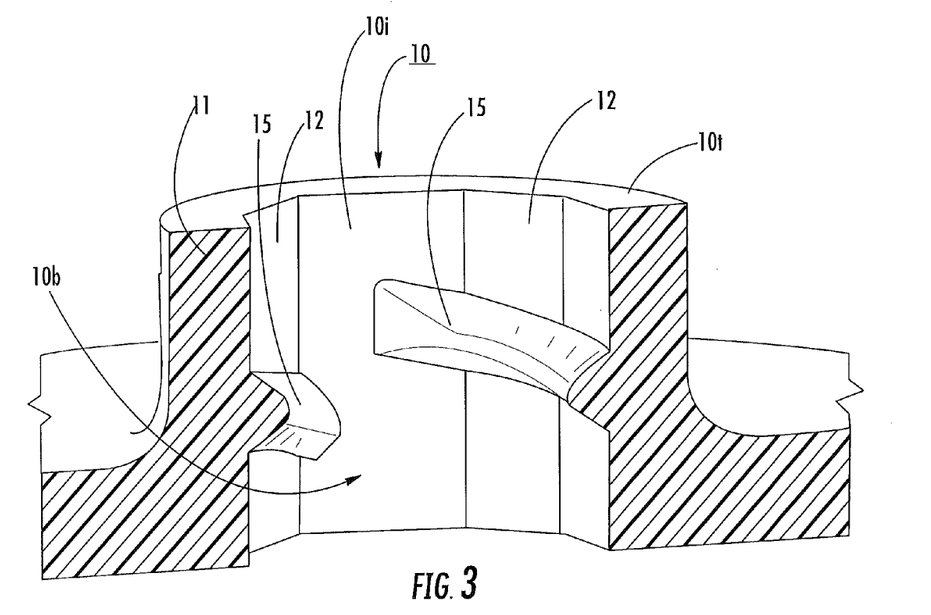
FIG. 3 is an enlarged section view of the tip or neck of the adapter cap shown in FIG. 1 according to embodiments of the present invention.
Figure 4:
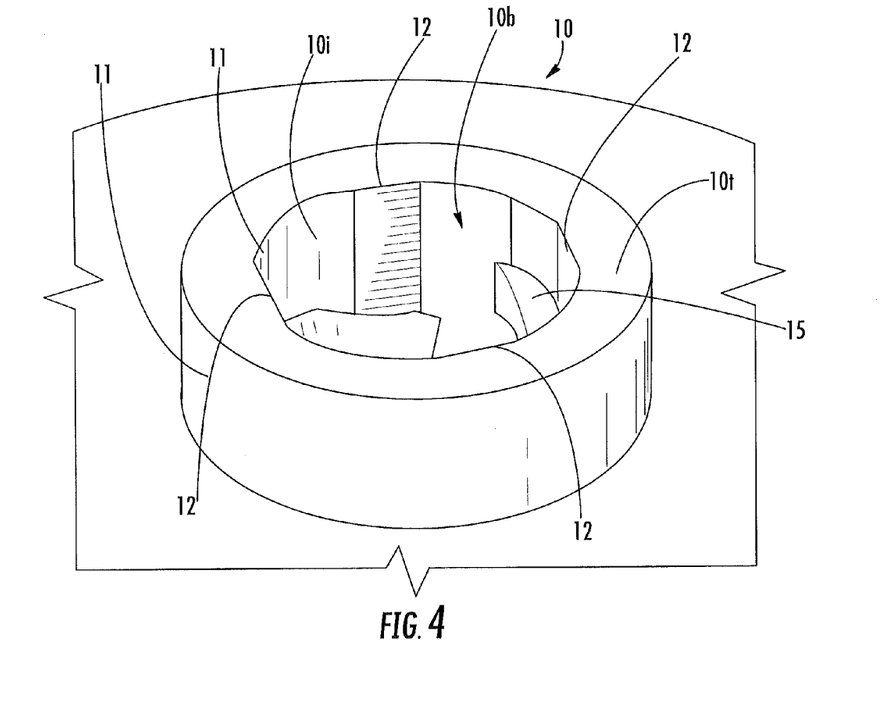
FIG. 4 is an enlarged top perspective view of the adapter cap shown in FIG. 1.

As shown in FIGS. 3 and 6, for example, the flat surfaces 12 can extend above and below the threads 15. The flat surfaces 12 typically extend continuously above the threads 15 up to the end of the tip 10t of the cap 10. The flat surfaces 12 can have the same length and width and can be symmetrically circumferentially distributed. In other embodiments, the flat surfaces 12 can be asymmetrically positioned and/or have different widths and lengths.

In some embodiments, two flat surfaces 12 can be closer together than another one or more flat surfaces 12. In some embodiments, two or more flat surfaces 12 can reside on one side of the needle bore 10b wall and none on the diametrically opposing other side or two can reside on one side and one, two and three on the diametrically opposing side of the needle bore 10b.

As shown in FIG. 7, for example, the flat surfaces 12 project out a small distance "D$_1$" from adjacent segments 13 of the inner surface 10i of the wall 11 of the cap 10. The small distance can be such as between about 0.10-0.20 mm, average, typically between about 0.10 and 0.12 mm, average, to define segments with increased wall thicknesses (e.g., a wall thickness of about 1.0 mm in a non-flat inner wall segment transitions to a wall thickness of about 1.10 mm at the flat surface). The flat surfaces 12 can have different thicknesses or the same thicknesses. Diametrically opposed flat surfaces 12 can be spaced apart a distance D$_2$, which may be between about 3 mm to about 5 mm, typically about 4.4 mm, average.

As also shown in FIG. 7, in some particular embodiments, the flat surfaces 12 are four flat surfaces, spaced apart at 90 degrees from each other (the broken line arrows are drawn with respect from the centerline of the needle bore 10b to a center of each of the flat surfaces 12).

Figure 8:
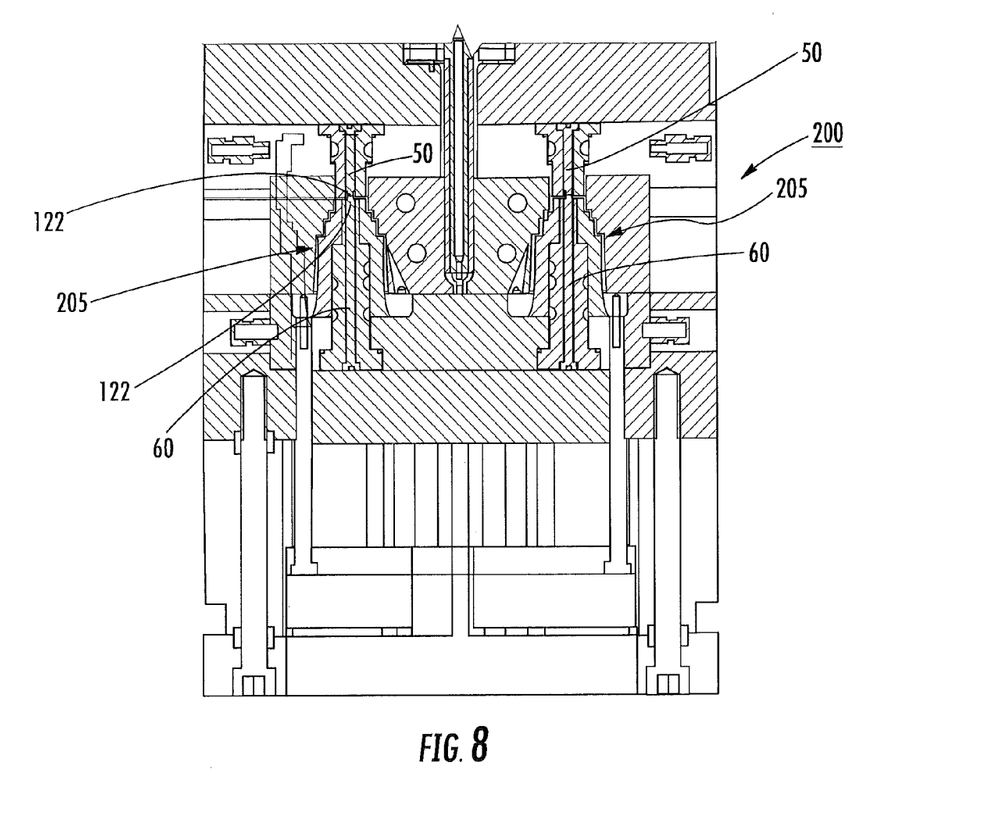
FIG. 8 is a partial section view of an injection mold assembly according to embodiments of the present invention.

FIG. 8 illustrates an example of an injection mold assembly 200 that can be used to form adapter caps 10. The injection mold assembly 200 includes at least one injection mold cavity 205 that is configured to provide the desired outerwall shape of the adapter cap 10. The mold cavity 205 can also cooperate with at least one pin 50, 60 that extends through a center region of the respective mold cavity to form the flat surfaces 12 on the internal needle bore of the cap 10. In the embodiment shown in FIG. 8, there are two longitudinally aligned pins, a core pin 60 and a cavity pin 50, but a single pin may be used or more than two pins.

In the embodiment shown in FIG. 8, mold assembly 200 includes a plurality of adjacent mold cavities 205 for concurrently injection molding a plurality of adaptor caps 10, e.g., a block of eight, two rows of four mold cavities.

Figure 9:
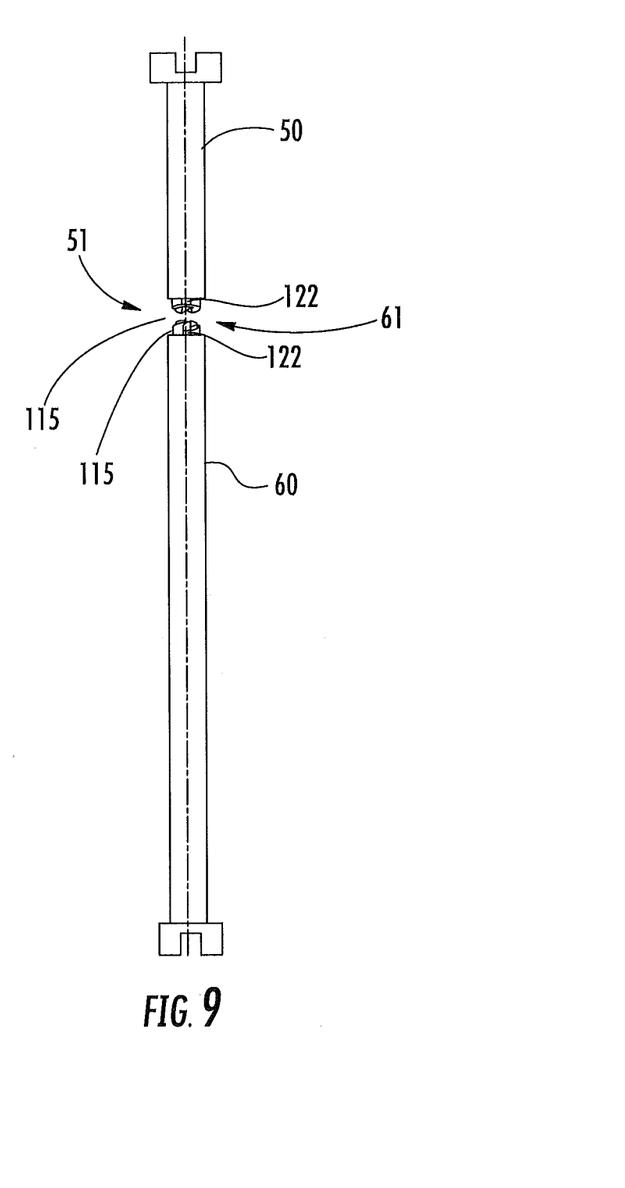
FIG. 9 is a side view of two cooperating pins that can be used in the mold assembly shown in FIG. 8 according to embodiments of the present invention.

FIG. 9 illustrates an exemplary configuration of cavity and core pins 50, 60, each with a reduced diameter end portion 51, 61 having a tip with a thread configuration 115. One or both pins 50, 60 can include a plurality of circumferentially spaced apart longitudinally extending flat surfaces 122 on the reduced diameter end portion 51, 61 with a reduced nominal diameter relative to adjacent wall segments. The reduced nominal diameter can be between about 0.1 mm to about 0.2 mm less than a neighboring non-flat segment. The plurality of flat surfaces 122 can be between 2-10 and can have similar or corresponding widths, lengths and configurations of the flat surfaces 12 of the adapter cap 10 described above.

Figure 10:
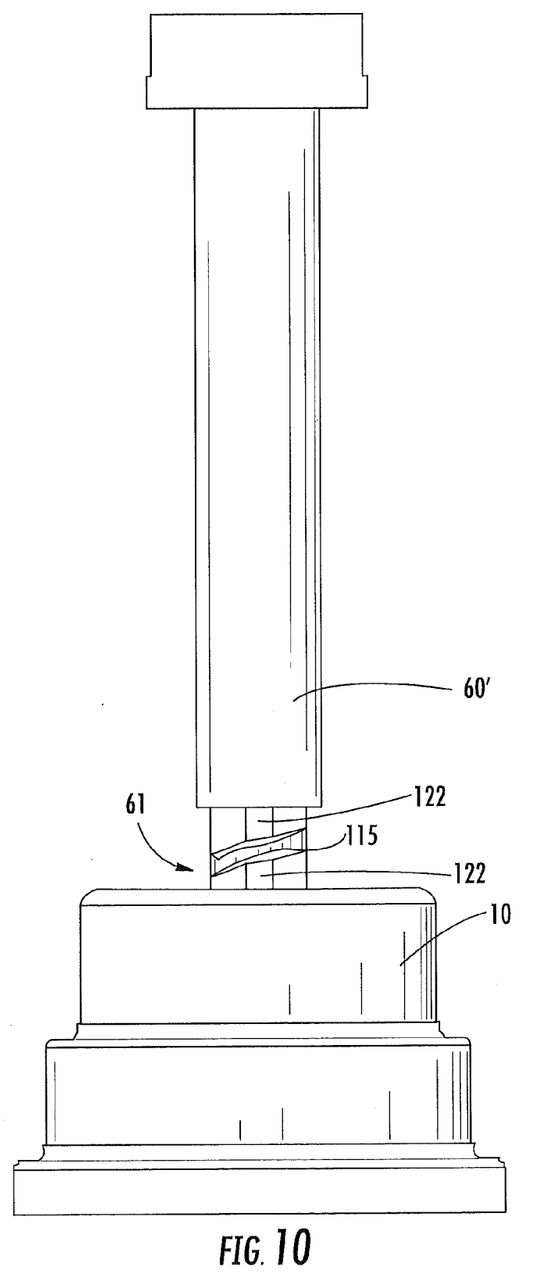
FIG. 10 is a side view of another embodiment of a core pin that can be used in the injection mold assembly according to embodiments of the present invention.

FIG. 10 illustrates another embodiment of a core pin 60' having a reduced diameter end portion 61 with longitudinally extending external flat surfaces 122 that extend above and below at least one thread segment 115.

The core pin 60, 60' can extend into the mold cavity 205 (FIG. 8) to form the needle bore features, e.g., thread(s) 115 and flat surfaces 12 without requiring the cavity pin 50.

The molding can be carried out to pull the pin 60, 60' straight out of the mold cavity and/or cap without requiring a spinning core for forming the needle bore threads thus reducing tooling costs and complexity.

FIG. 11 illustrates a sequence of operations that can be used to collect a blood sample in a collection/culture container 110 using a adapter cap 10 according to embodiments of the present invention. The adapter cap 10 can be provided with the needle 150 and tube 151 pre-attached to the cap 10 or a user can attach the needle 150 at the draw site (labeled in step 3). As is known, a needle is inserted into a vein (venipuncture) and the adapter cap with needle 150 held therein is pressed onto a container 110 whereby blood is drawn into the container 110. An insert 300 can be used to draw blood into another container or to cooperate with a vacuum collection tube (step 7).

In some embodiments, the sealed collection/culture containers 110 are typically substantially impermeable and typically have oxygen transmission rates ("OTR") (cubic centimeter/day/atm air) that are between 0.0001 to about 0.01 or 0.04 after manufacturing and throughout at least a one year shelf life, typically a 1-2 year shelf life. The test conditions for OTR can be at 1 atm, a relative humidity ("RH %") that is 40% and a room temperature that is 20 degrees C. The term "day" means 24 hours. The OTR can be determined using MOCON Oxytran 2/61 Oxygen Permeability Instrument via ASTM F-1307 or other suitable instruments and protocols. An accelerated age test can be carried out at 80 degrees C. for seven (7) days. The age test is typically carried out after the container has been filled with sensor and growth media, sealed and autoclaved.

FIG. 11 illustrates an exemplary sample culture container 110. The container 110 can have a body shape in the form of a standard culture bottle (e.g., a blood culture bottle). However, the description of a culture bottle (e.g., a blood culture bottle) is offered by way of example and not limitation. As shown, the containers 110 are elongated containers with an internal volume and an outer wall having an outermost width dimension (W) being less than a height dimension (H). In some embodiments, the height (H) is greater than twice the width (W), e.g., H>2W. In some embodiments, the containers have tubular bodies with maximum outer diameters between about 1-2 inches and heights of between about 2-5 inches. In some particular embodiments, the containers 110 have an outer diameter of about 1.36 inches (34.6 mm) and a height that is about 4.68 inches (119 mm).

The container 110 may include a bar code label (not shown) for automated reading of patient data and/or test parameters of the content of the container 110. In some embodiments, the top portion of the container 110 can include a narrow portion or neck 112. The container 110 may also include an elastomeric stopper optionally having a self-(re)sealing pierceable material and/or septum.

The container 110 can have a headspace that can accommodate a target (non-air) gas or gas mixture. The gas in the headspace can be introduced into the container 110 during manufacture. The gases introduced into the container could be oxygen, nitrogen, carbon dioxide, helium, or combination of these gases. The gas could be introduced into the container at a vacuum. The vacuum can be between 3-20 inch Hg, such as about 4.5 inch, about 8 inch, or about 17 inch Hg.

In some embodiments, the container 110 may also have an internal sensor 120 (e.g., a Liquid Emulsion Silicone "LES" sensor) formed or placed in the bottom portion of the container 110 for purposes of visual/optic detection of the internal content (e.g., such as via a colorimetric or fluorescent sensor), to detect the presence of microbial or other growth in the container 110. The container 110 can include a body with an optically/visually transmissive material.

A variety of sensor technologies are available in the art and may suitable. In some embodiments, the detection unit takes colorimetric measurements as described in the U.S. Pat. Nos. 4,945,060; 5,094,955; 5,162,229; 5,164,796; 5,217,876; 5,795,773; and 5,856,175, which are incorporated by reference as if recited in full herein. A positive container can be identified depending upon these colorimetric measurements, as explained in these patents. Alternatively, detection could also be accomplished using intrinsic fluorescence of the microorganism, and/or detection of changes in the optical scattering of the media (as disclosed, for example, in co-pending U.S. patent application Ser. No. 12/460,607, filed Jul. 22, 2009 and entitled, "Method and System for Detection and/or Characterization of a Biological Particle in a Sample"), which is also incorporated by reference as if recited in full herein. In yet another embodiment, detection can be accomplished by detecting or sensing the generation of volatile organic compounds in the media or headspace of the container.

Exemplary analytical instruments for analyzing the bottles for presence of organisms include U.S. Pat. Nos. 4,945,060; 5,094,955; 6,709,857 and 5,770,394, U.S. Patent Publication 2011/0124028 and PCT Publication WO 94/26874. The contents of these documents are hereby incorporated by reference as if recited in full herein. As described in more detail in U.S. Patent Publication 2011/0124028 incorporated by reference hereinabove, an automated detection system may contain one or more work-flow stations for obtaining one or more measurements, readings, scans and/or images of a specimen container, thereby providing information, such as container type, container lot number, container expiration date, patient information, sample type, test type, fill level, weight measurement, and the like.

The container 10 may further comprise a growth or culture medium or promoting and/or enhancing microbial or microorganism growth. The use of a growth or culture media (or medium) for the cultivation of microorganisms is well known. A suitable growth or culture medium provides the proper nutritional and environmental conditions for growth of microorganisms and should contain all the nutrients required by the microorganism which is to be cultivated in the specimen container 110. The growth media can comprise culture growth media for enhancing or promoting microorganism growth. The media can include a growth media for an aerobic organism or an anaerobic organism.

The adapter cap 10 and container 110 can include a body 10b, 110b that is molded. The body 10b and 110b can be a molded polymeric body (e.g., a thermoplastic material body) made from a single layer of polymeric (plastic) monolithic material. The adapter cap 10 can be formed of polypropylene of between about 1-2 mm.

One of the exemplary uses of the containers 110 is in culturing a test sample to detect microbial growth in test sample (e.g., a blood sample).

The present invention is explained in greater detail in the following non-limiting Examples.

EXAMPLES

Example 1

Figure 12A:
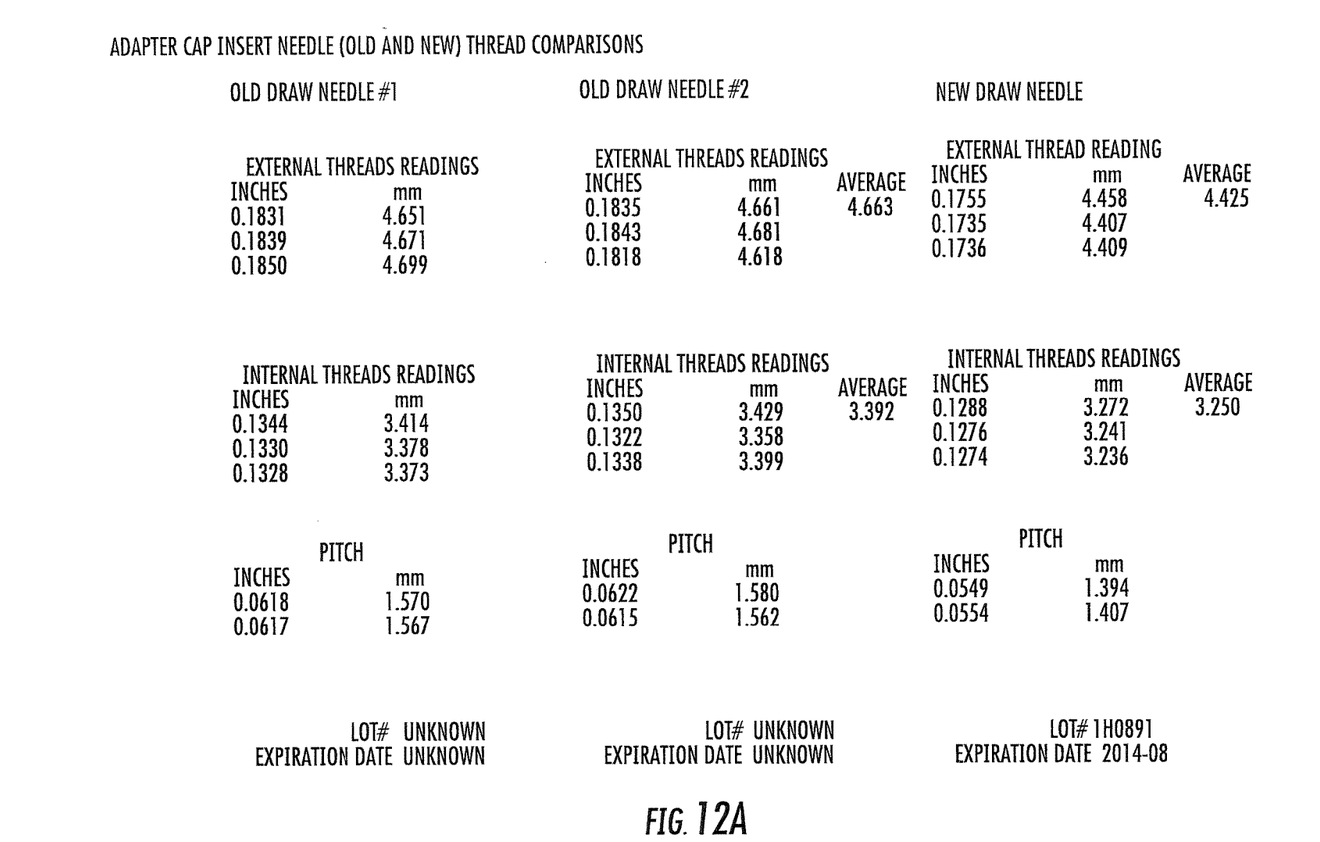
FIGS. 12A and 12B are tables of different measured dimensions of external and internal threads and pitches of various adaptor cap insert needles. The "New Draw" measurements show examples of dimensional variation that can be successfully accommodated by adapter caps having internal flat surfaces and threads according to embodiments of the present invention.
Figure 12B:
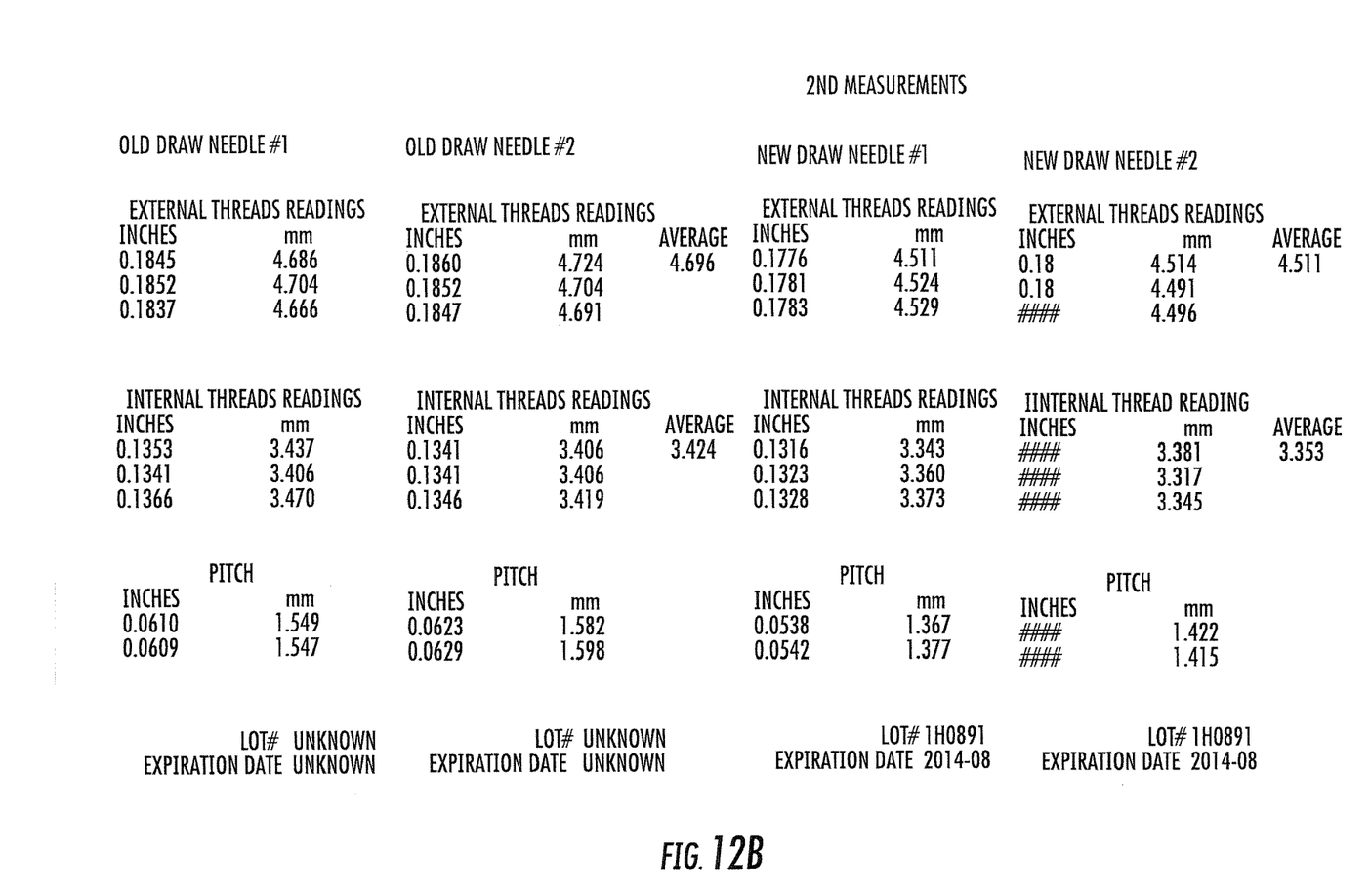

FIGS. 12A and 12B are tables of different dimensions of external and internal threads and pitches of two different versions of a Becton Dickenson (BD) cap insert needle (the needles refer to the BD Vacutainer Safety Lok Blood Collection Kit Reference No. 367283, 23G×¾"×12"). The "New Draw" headers refer to draws undertaken with the noted "new" draw needle and the new adaptor cap with the flat surfaces and the threads in the needle bore. The "Old Draw" headers refer to draws undertaken with an older version of the BD draw needle with larger dimensions from the newer needle configuration. The adaptor cap with the addition of the flat surfaces in the needle bore was found to be able to successfully engage the new smaller insert needle.

Table 1 below is a list of needle sets that were tested with the adapter cap with flat surfaces and threads to verify the different manufacturer needle sets were able to successfully engage the new adapter cap.

TABLE 1

BacT/Alert Plastic Bottle Adaptor Cap w/needle set listed below

Greiner Bio-One Vacuette Safety BloodCollection Set with Holder, REF 450184
Greiner Bio-One Vacuette Safety Blood Collection Set, REF 450095
Myco VAKU-8+ Safety Blood Collection System/Infusion Set, REF SVMSP-23L
Sarstedt Safety-Multifly-Set, REF 85.1638.200
BD Vacutainer Safety-Lok Blood Collection Set, REF 367283
BD Vacutainer Multiple-Sample Luer Adapter, REF 367290
Kawasumi K-Shield Winged Needle BloodCollection Set, REF DBM1-23G
Terumo Surshield Safety Winged Blood Collection Set, REF MN-SV521B3
BD Vacutainer Safety-Lok Blood Collection Set, REF 367281

The foregoing is illustrative of embodiments of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accord- That which is claimed:

1. An adapter cap for a sample collection container, comprising:
a monolithic elongate body having an upper neck portion with an open needle bore, wherein the upper neck portion merges into a larger lower body portion with an open internal cavity configured to receive a sample collection container, wherein the needle bore has a downwardly extending wall with an inner surface that comprises (i) a plurality of circumferentially spaced apart longitudinally extending flat surfaces and (ii) first and second circumferentially spaced apart threads that extend radially inward from the inner surface so that respective innermost edges reside on opposing sides of an axially extending centerline of the elongate body, and wherein at least some of the plurality of circumferentially spaced apart longitudinally extending flat surfaces are separated by neighboring wall segments having a different wall thickness than the wall segments comprising the flat surfaces.

2. The adapter cap of claim 1, wherein the upper neck portion has a circular outer perimeter and merges into the larger lower body portion, and wherein the upper neck portion is concentrically aligned with the open internal cavity.

3. The adapter cap of claim 1, wherein the flat surfaces extend a distance above and below the threads.

4. The adapter cap of claim 3, wherein the threads have a respective injection molded thread configuration and the thread on one side of the needle bore resides above the thread on an opposing side of the needle bore, and wherein the first and second threads circumferentially extend only about a sub-portion of a circumference of the inner wall.

5. The adapter cap of claim 1, wherein the plurality of flat surfaces is between 2-6 flat surfaces, wherein the plurality of flat surfaces project outward a distance from the inner surface of the downwardly extending wall so that the wall segments with the flat surfaces have a greater wall thickness than the neighboring wall segments, and wherein the downwardly extending wall of the upper neck portion of the needle bore is cylindrical.

6. The adapter cap of claim 1, wherein the elongate body comprises a molded polymeric material with a substantially constant wall thickness of between about 0.5 mm to about 2 mm.

7. The adapter cap of claim 6, wherein the wall thickness of the elongate body is about 1 mm, and wherein the polymeric material is polypropylene.

8. The adapter cap of claim 1, wherein the wall segments with the flat surfaces define wall segments with increased wall thickness of between 0.01 mm and 0.03 mm, average, relative to the neighboring wall segments.

9. The adapter cap of claim 1, wherein the plurality of longitudinally extending flat surfaces are four flat surfaces that are symmetrically circumferentially spaced apart.

10. The adapter cap of claim 1, wherein the plurality of longitudinally extending flat surfaces have a common substantially constant width that is between about 5%-30% of a major diameter of the needle bore.

11. The adapter cap of claim 1, wherein the needle bore has a major diameter of about 4.60 mm, and wherein the plurality of longitudinally extending flat surfaces have a width that is between about 0.25 mm to about 1 mm.

12. The adapter cap of claim 1, wherein at least some of the flat surfaces have a length of between about 2-2.8 mm.

13. The adapter cap of claim 1, wherein the needle bore has a major diameter of about 4.60 mm, and wherein opposing pairs of the plurality of longitudinally extending flat surfaces have a thickness sufficient to define a nominal diameter therebetween of about 4.40 mm.

14. The adapter cap of Claim 1 in combination with a culture collection container with an upper portion thereof residing in the open internal cavity of the larger lower body portion under the needle bore.

15. An adapter cap for a sample collection container, comprising:
a monolithic elongate body having an upper neck portion with an internal bore, wherein the upper neck portion merges into a larger lower body portion with an open internal cavity configured to receive a sample collection container, wherein the upper neck portion has a downwardly extending cylindrical outer wall with an inner surface providing the internal bore, wherein the inner surface comprises (i) a plurality of circumferentially spaced apart longitudinally extending flat surfaces that are separated by neighboring wall segments of lesser wall thickness and (ii) first and second circumferentially spaced apart threads that extend radially inward from the inner surface and extend only partially about a circumference of the internal needle bore, and wherein respective innermost edges of the threads reside on opposing sides of an axially extending centerline of the elongate body.

16. The adapter cap of claim 15, wherein the plurality of longitudinally extending flat surfaces have a common substantially constant width that is between about 5%-30% of a major diameter of the internal bore.

17. The adapter cap of claim 15, wherein the internal bore has a major diameter of about 4.60 mm, and wherein the plurality of longitudinally extending flat surfaces have a width that is between about 0.25 mm to about 1 mm.

18. The adapter cap of claim 15, wherein at least some of the flat surfaces have a length of between about 2-2.8 mm.

19. A method of fabricating an adaptor cap, comprising:
providing an injection mold cavity;
placing a core pin in the mold cavity, wherein the core pin has an end portion with a plurality of longitudinally extending spaced apart flat surfaces and a thread configuration;
introducing a moldable polymer material into the injection mold cavity having the core pin;
injection molding a monolithic adapter cap of claim 1; and
using a straight pull to remove the core pin thereby exposing the injection molded adapter cap with the needle bore without requiring spinning to form the threads to fabricate the adaptor cap.

20. The method of claim 19, further comprising placing a cavity pin in the mold cavity aligned with the core pin before the injection molding, wherein the cavity pin has a plurality of longitudinally extending spaced apart flat surfaces and a thread configuration.

21. The method of claim 19, wherein the injection molding is carried out to form the needle bore having the plurality of longitudinally extending flat surfaces so that the plurality of longitudinally extending flat surfaces extend above and below the threads.

* * * * *